(12) United States Patent
Headstrom

(10) Patent No.: US 8,970,072 B2
(45) Date of Patent: Mar. 3, 2015

(54) MAGNETIC SPRING SYSTEM FOR USE IN A RESONANT MOTOR

(75) Inventor: Patrick Headstrom, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 264 days.

(21) Appl. No.: 12/808,486

(22) PCT Filed: Nov. 18, 2008

(86) PCT No.: PCT/IB2008/054837
§ 371 (c)(1),
(2), (4) Date: Jun. 16, 2010

(87) PCT Pub. No.: WO2009/081295
PCT Pub. Date: Jul. 2, 2009

(65) Prior Publication Data
US 2010/0306934 A1 Dec. 9, 2010

Related U.S. Application Data

(60) Provisional application No. 61/015,071, filed on Dec. 19, 2007.

(51) Int. Cl.
*H02K 33/00* (2006.01)
*A46B 13/00* (2006.01)
(Continued)

(52) U.S. Cl.
CPC ............... *F16F 6/005* (2013.01); *A61C 17/221* (2013.01); *H02K 33/06* (2013.01)
USPC ................... 310/15; 310/30; 310/36; 15/22.2

(58) Field of Classification Search
CPC ............................... H02K 33/00; H02K 33/06
USPC .......... 310/14, 15–39; 15/22.2; 335/229, 234, 335/207
IPC ............................................ H02K 33/06, 33/12
See application file for complete search history.

(56) References Cited

U.S. PATENT DOCUMENTS 3,129,347 A * 4/1964 Tullio Tognola ............... 310/15
3,728,654 A * 4/1973 Tada .............................. 335/234
(Continued)

FOREIGN PATENT DOCUMENTS

BE 888229 A1 10/1981
JP 54094812 A1 7/1979
(Continued)

OTHER PUBLICATIONS

JPO Machine Translation, JP 11168869 A, Vibration Generator, Mar. 7, 2012, http://dossier.ipdl.inpit.go.jp/text_trans.html.*
(Continued)

*Primary Examiner* — Quyen Leung
*Assistant Examiner* — Thomas Truong

(57) ABSTRACT

A magnetic spring arrangement for a resonant motor including a housing, magnets fixed in position at opposing ends of the housing, a magnet positioned within the housing for movement toward and away from the fixed magnets in a reciprocal oscillating motion with a driving action produced by a stator coil and an AC drive signal, wherein an applicator member is attachable to the moving magnet for corresponding movement of a workpiece portion of the applicator member.

7 Claims, 4 Drawing Sheets

(51) Int. Cl.
*F16F 6/00* (2006.01)
*A61C 17/22* (2006.01)
*H02K 33/06* (2006.01)

(56) References Cited

U.S. PATENT DOCUMENTS

| | | | | |
|---|---|---|---|---|
| 3,968,387 | A * | 7/1976 | Scarff | 310/16 |
| 4,129,187 | A | 12/1978 | Wengryn | |
| 4,531,820 | A | 7/1985 | Petersen | |
| 5,434,549 | A * | 7/1995 | Hirabayashi et al. | 335/229 |
| 5,809,157 | A * | 9/1998 | Grumazescu | 381/412 |
| 5,818,132 | A | 10/1998 | Konotchick | |
| 6,040,752 | A | 3/2000 | Fisher | |
| 6,693,787 | B2 | 2/2004 | Kolmanovsky | |
| 7,288,860 | B2 * | 10/2007 | Cheung et al. | 310/12.12 |
| 2004/0128781 | A1 * | 7/2004 | Kunita et al. | 15/22.2 |
| 2006/0208600 | A1 * | 9/2006 | Sahyoun | 310/254 |
| 2008/0001484 | A1 * | 1/2008 | Fuller et al. | 310/15 |
| 2008/0074083 | A1 * | 3/2008 | Yarger et al. | 320/137 |

FOREIGN PATENT DOCUMENTS

| | | | | |
|---|---|---|---|---|
| JP | 06315255 | A * | 11/1994 | H02K 33/16 |
| JP | 11168869 | A1 | 6/1999 | |
| JP | H11197160 | A | 7/1999 | |
| JP | 2006280156 | A | 10/2006 | |

OTHER PUBLICATIONS

Machine Translation, JP 06315255 A, Nov. 8, 1994.*
Qian, Kun-Xi et al "Novel Magnetic Spring and Magnetic Bearing" IEEE Transactions on Magnetics, vol. 39, No. 1, Jan. 2003, pp. 559-561.
Machine Design "Magnets Replace Gas in Springs" , Apr. 4, 2002.
Machine Design: Magnets Replace Gas in Springs; Copyright 2002 Penton Media, Inc. 2 Page Document, Downloaded From http://license.icopyright.net/user/viewFreeUse.act?fuid=NTI2MjUx on Oct. 26, 2007.
Qian et al: "Novel Magnetic Spring and Magnetic Bearing"; IEEE Transactions on Magnetics, Vol. 39, No. 1, Jan. 2003, pp. 559-561.

* cited by examiner

MAGNETIC SPRING SYSTEM FOR USE IN A RESONANT MOTOR

TECHNICAL FIELD

This invention relates generally to resonant motors which produce an oscillating output action, and more particularly concerns such a motor using magnetic action as an alternative to conventional springs.

BACKGROUND OF THE INVENTION

In resonant motors which produce an oscillating output action, metal springs are part of the motor contributing to the action. However, after a large number of successive uses, the springs develop metal fatigue, resulting in reduced performance and eventual breakage. The problem of metal fatigue in the springs is particularly prevalent in systems which operate at high frequency and hence have a large number of stress cycles. In addition, metal springs have space limitations relative to a desired output stroke, since for a given degree of desired movement, i.e. 1 millimeter, for example, of a workpiece, approximately five times that distance is required between the opposing masses for the mechanical springs.

It would hence be desirable to have a motor arrangement which produces a desired motor output but without having major components which are subject to fatigue stresses and failures.

DISCLOSURE OF THE INVENTION

Accordingly, a resonant linear motor, using a magnetic spring system, comprising: a housing; two permanent magnets fixedly positioned at opposing ends of the housing; and at least one permanent magnet positioned in the housing for movement toward and away from each end magnet in a reciprocal oscillating motion, wherein the polarities of the moving magnet oppose the polarities of the fixed magnets, wherein a workpiece assembly is attachable to the moving magnet, and extends out through one of the fixed magnets, for linear movement thereof, in response to a driving action for the motor.

Also disclosed is a resonant motor using a magnetic spring system for oscillating rotational action, comprising: a housing; a center element mounted for rotation about a central axis, the center element having magnets positioned on opposing sides thereof with opposing polarities facing outwardly therefrom, wherein the center element has a workpiece assembly extending therefrom for rotational action of the workpiece; fixed magnets positioned adjacent an outer surface of the center element; and a drive assembly with an AC drive signal for driving the center element, wherein the polarities of the fixed magnets are such relative to the polarities of the magnets on the center element, that there is a magnetic interaction between the fixed magnets and the mounted magnets, resulting in an oscillation of the center element, the motor characterized by the absence of mechanical springs.

BEST MODE FOR CARRYING OUT THE INVENTION

Figure 1:
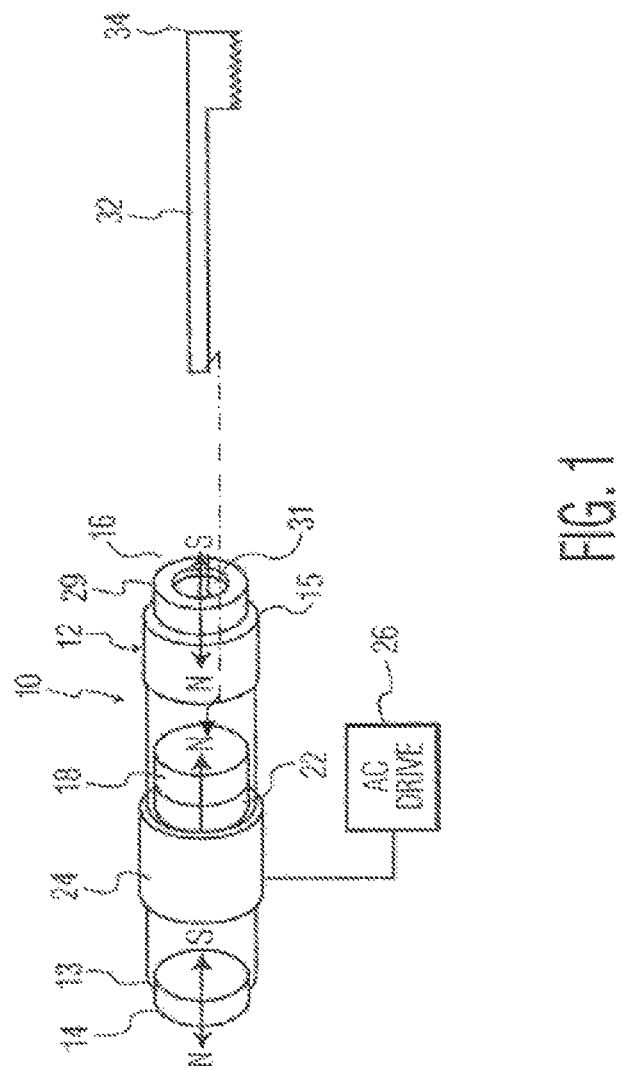
FIG. 1 is a perspective view of one embodiment of a motor system and application using magnetic action as an alternative to springs.
Figure 2:
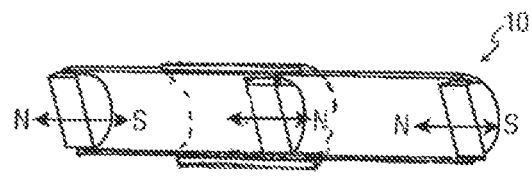
FIG. 2 is a longitudinal cross-sectional view of the motor system of FIG. 1.

FIGS. 1 and 2 show a linear motor 10 which includes a magnetic action arrangement as an alternative to the conventional metal spring action to accomplish a linear output motion. The motor 10 includes a housing 12 which in the embodiment shown is in the form of a tube, although it could have other cross-sectional configurations. Fixedly mounted at the respective ends 13 and 15 of the housing are permanent magnets 14, 16, in the form of discs, having north and south polarity faces, as shown. One magnet 14 has its north polarity facing outward from end 13 of the housing, while the opposing magnet 16 has an opposing arrangement, i.e. the south polarity faces outwardly from end 15 of housing 12.

A third magnet 18 is positioned internally of the housing between magnets 14 and 16. The north polarity face of magnet 18 faces the north polarity of magnet 16 in a repelling action, while the south polarity face of magnet 18 faces the south polarity of magnet 14, also in a repelling mode. Magnets 14, 16 and 18 are conventional permanent magnets, and in the embodiment shown are discs of magnetic material approximately 4 mm thick, although this dimension can be varied.

Magnet 18 is positioned for sliding movement within housing 12. In one embodiment, a sliding linear bearing 22 is used, but other types of linear bearings can also be used. The linear bearing 22 reduces energy loss, i.e. by friction, during the movement of magnet 18 within the housing during operation of the motor.

A coil 24 is wrapped around the outside of housing 22 in the vicinity of the moving magnet 18 when it is at rest. For instance, coil 24 could be approximately midway along the length of the housing, although this is not necessary to the operation of the apparatus. Coil 24 is driven by an AC signal source 26, which actuates the moving magnet in an oscillating manner along the housing between magnets 14 and 16, although magnet 18 will typically not contact magnets 14 and 16 due to the magnetic repelling action between them. The magnetic action simulates two metal springs positioned between three masses (2 fixed, 1 moving) in the housing.

Thus, coil 24 functions like a stator in a conventional motor, while moving magnet 18 functions as an armature. Other arrangements to move magnet 18 within the housing could be used. In operation, the AC current provided by circuit 26 actuates the moving magnet 18 in an oscillating manner, such that as the magnet is driven in one direction, it comes close to the magnet at that end of the housing, at which point it is repelled, and the AC drive signal reverses, moving magnet 18 in the other direction. This action is repeated continuously for as long as the AC signal is provided.

The frequency of the AC signal is set to be near the resonant frequency of the spring mass system which in this case is the mass of the moving magnet and the repulsion force between the magnets, which is similar to the spring action as the springs compress and expand in operation. The moving magnet 18 will achieve a peak amplitude (movement) at the point of the system's greatest efficiency, i.e. at or near the spring mass resonant frequency of the spring mass system. Typically, this could be ±30 Hz or closer.

The motor discussed above can have a number of applications. For instance, in FIG. 1, one of the magnets, e.g. magnet 16, could be a ring magnet 29, with a central opening 31. This permits an actuator arm 32 to be connected to the moving magnet 18 and extend from the end of the housing. At the end of actuator arm 32 is a workpiece 34. Actuator arm 32 is typically supported within ring magnet 16 by a bearing, which permits linear motion of the actuator arm. Various linear work applications can be carried out with such an arrangement. For instance, workpiece 34 could be a brushhead, providing a linear toothbrush action. Other linear actions could be accomplished, such as a high-speed firing action, or used in various toys, including a pogo stick or trampoline, or in other appliances requiring a linear movement. A significant advantage of the above motor arrangement is the elimination of certain parts, e.g. metal springs, subject to fatigue, although the linear bearing may be subject to some wear.

Figure 3:
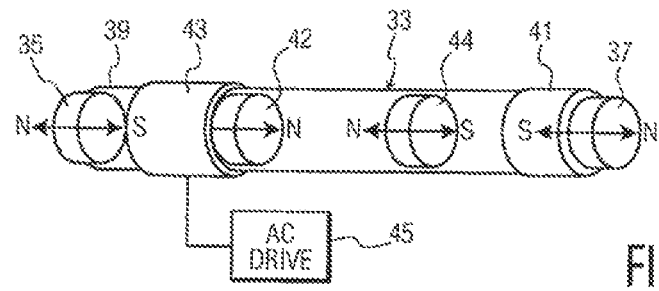
FIG. 3 is a perspective view of another embodiment of the motor system.

FIG. 3 shows another embodiment which includes a housing 33, and two magnets with opposing polarities 35 and 37 at the opposing ends 39, 41 of the housing. In this embodiment, however, there are two magnets 42, 44 positioned within housing 33. This produces the effect of three magnetic springs within the housing. The embodiment also includes a coil 43 around the exterior of housing 33, along with an AC drive signal source 45. The polarities of the magnets are arranged such that the moving magnets are repelled at both faces thereof. The advantage of this system is that the opposing movement of the two moving magnets cancels vibration. The system of FIG. 3 is driven at a frequency at or near (.+−.30 Hz or closer) the resonant frequency of the spring mass system to achieve the most efficient driving arrangement.

Figure 3A:
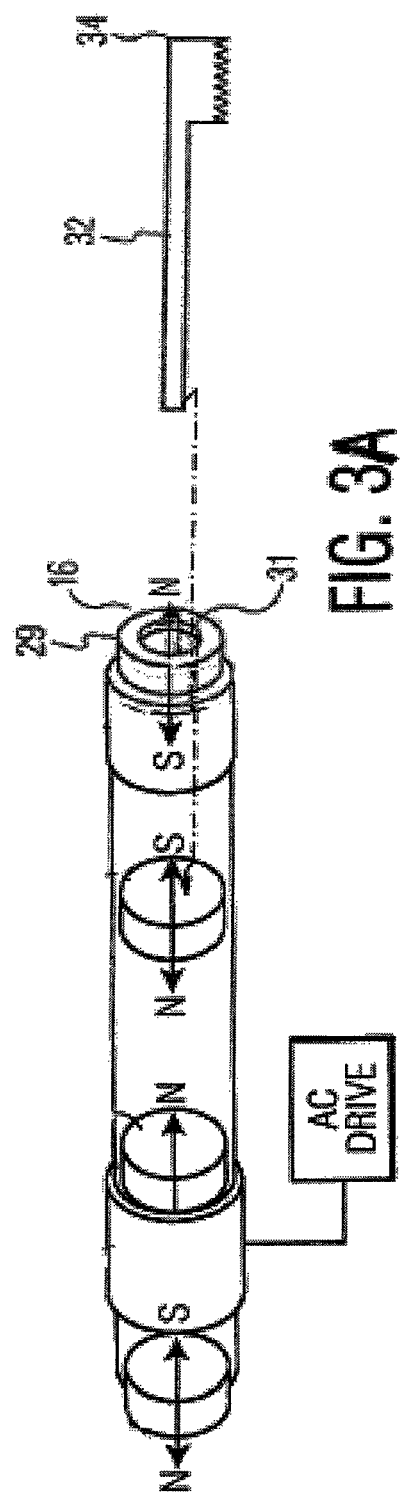
FIG. 3A is a perspective view of the embodiment of the motor system of FIG. 3.

FIG. 3A shows the embodiment of FIG. 3 including the magnet 16 being the ring magnet 29 with the central opening 31. As previously discussed, this permits the workpiece 34 through the actuator arm 32 to be connected to one of the two moving magnets and extend from the end of the housing.

The motor of FIGS. 1-3 can have various configurations. It can be somewhat elongated, as shown, or short and wider. With this magnetic motor arrangement, the stroke length that is desired for the workpiece can be approximately the same as the length of the magnetic spring, i.e. the distance between the moving magnet and the end magnets. Hence, there is not the space requirement of a conventional steel spring arrangement.

Figure 4:
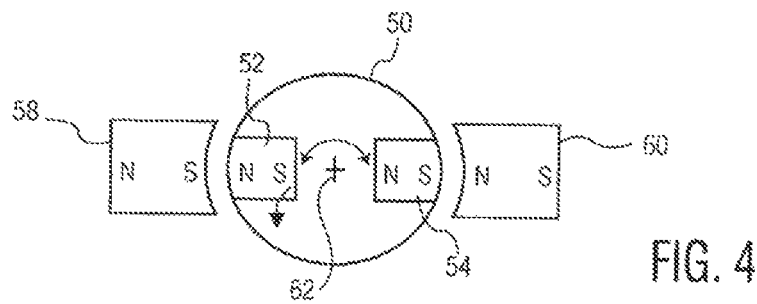
FIGS. 4 and 5 are cross-sectional views of a magnetic action motor system with radial magnet placement.
Figure 5:
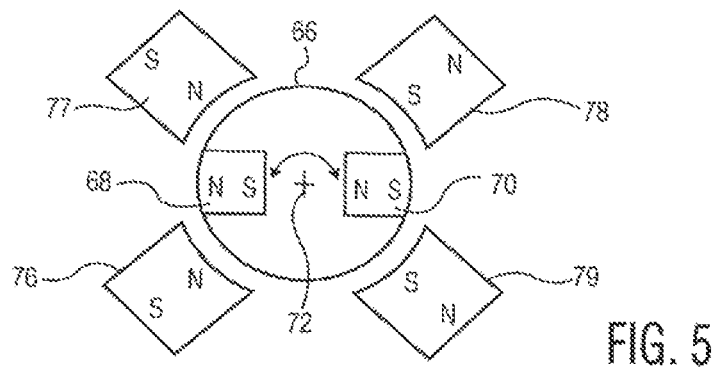

Besides producing a linear workpiece motion, the system can be arranged with magnetic action to accomplish a rotational output motion as well. Two such embodiments are shown in FIGS. 4 and 5. FIG. 4 is a cross-sectional diagram of one arrangement for rotational action in which magnets are positioned radially. A center element 50 has two magnets 52, 54 on opposing sides thereof, one magnet 52 having a north polarity facing outwardly, while the opposing magnet 54 has a south polarity facing outwardly. Positioned adjacent the center element 50 are two fixed permanent magnets 58 and 60. In equilibrium, magnet 58 has its south pole aligned in attraction with the north pole of magnet 52, while fixed magnet 60 has its north pole aligned in attraction with the south pole of magnet 54. This arrangement is based on magnetic attraction, i.e. the magnets tend to align as shown. A stator assembly and an AC signal circuit (not shown) drive center element 52 rotationally, in an oscillating manner about center axis 62, away from the equilibrium position shown in FIG. 4. The frequency of the AC drive signal is set near to or at the resonant frequency of the spring-mass system to give maximum efficiency.

FIG. 5 shows another rotational arrangement. Mounted on the center element 66, which is mounted for rotation on axis 72, are two opposing permanent magnets 68, 70. Magnet 68 has its north pole facing outwardly, while magnet 70 has its south pole facing outwardly. Fixedly positioned at spaced points around the periphery of center element 66 are four permanent magnets 76, 77, 78 and 79. The position of magnets 76 and 77 is the mirror image of magnets 78 and 79. The angle between magnets 76 and 77 is in the range of 1-30°; the angle between magnets 78 and 79 is the same. The angle between the magnets will be determined based on the amplitude of motion desired. A 5°-30° range will accommodate a range of amplitude from 1°-15°. Higher amplitudes will require greater angles. In this arrangement, magnets 76 and 77 will have their north poles facing toward center element 66, while opposing magnets 78 and 79 will have their south poles facing center element 66. The equilibrium position of this arrangement is shown in FIG. 5, with the north pole of magnet 68 being equidistant between magnets 76 and 77 and the south pole equidistant between magnets 78 and 79, respectively.

As with the arrangement of FIG. 4, FIG. 5 will be driven with a stator circuit and an AC drive signal, which will oscillate the center element 66 through a specific angle. The interaction between magnets on the center element and the fixed magnets will tend to return the center element toward its equilibrium position shown in FIG. 5 from each end point of oscillation. The arrangement of FIG. 5, as well as the arrangements of FIGS. 1-3, and the arrangement of FIGS. 6 and 7A/7B which are yet to be described, is efficient, and further has the advantage that as the amplitude (the angle) of rotation increases, closing the magnetic gap, the spring rate of the spring mass system increases as well, which has advantages in that the system will self limit at the amplitude which produces a resonant frequency close to the drive frequency.

Workpiece elements can be mounted to the center element in the embodiments of FIGS. 4 and 5 for rotational action. Examples of rotational action applications include toothbrushes, stirring devices and massagers, among others.

Figure 6:
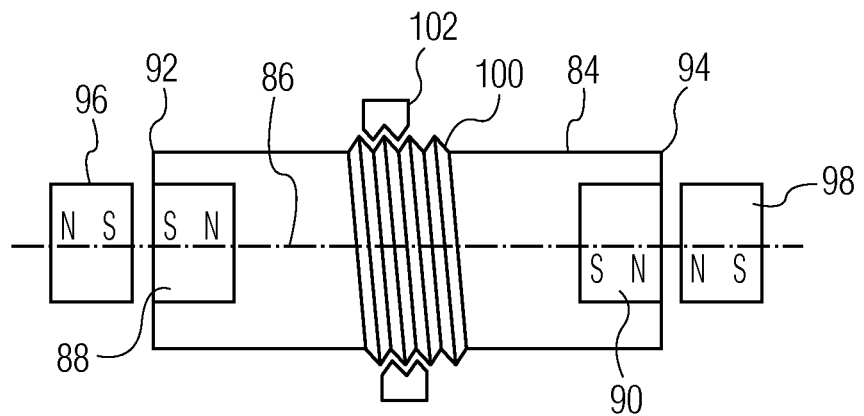
FIGS. 6 and 7 are elevational views of a magnetic action motor using axially positioned magnets.
Figure 7A:
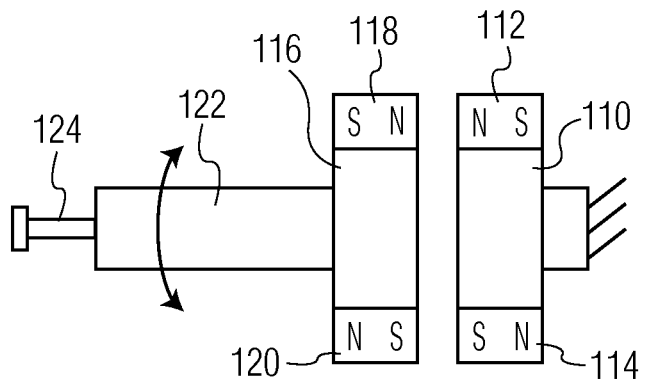
Figure 7B:
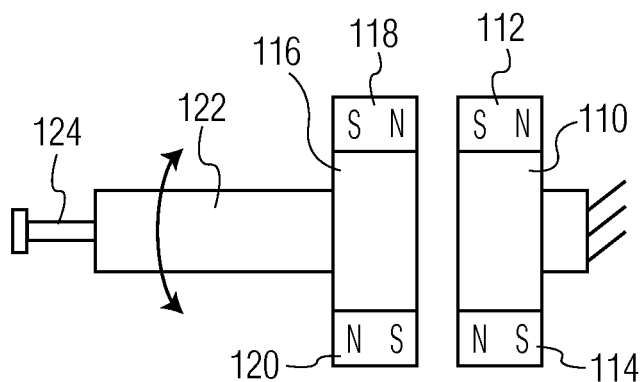

FIGS. 6 and 7A and 7B show additional embodiments for rotational action, with axial placement of the fixed magnets. In FIG. 6, a center cylindrical element 84 is rotatable about its longitudinal axis 86. At the ends 92, 94 of center element 84 are permanent magnets 88 and 90. Magnet 88 has its south pole facing outwardly, while magnet 90 has its north pole facing outwardly. Positioned adjacent the respective ends 92 and 94 of center element 84 are fixed permanent magnets 96 and 98. Magnet 96 has its south pole facing the adjacent south pole of magnet 88, while magnet 98 has its north pole adjacent the north pole of magnet 90. Center element 84 has a threaded portion 100 along its length with an external nut element 102 which is fixed in position. This arrangement works similar to the arrangement of FIG. 5, i.e. in a magnetic repulsion mode. As a stator element driven by an AC source rotates the center element, the thread and nut arrangement permit full rotation of the center element, tending to hold the center element in position while it is rotated. When the AC drive signal decreases in amplitude, the repulsion between the closely adjacent pair of one fixed magnet and one center element mounted magnet tends to provide assistance for reversing rotation of the center element as the AC signal goes to the opposing polarity.

FIG. 7A shows a magnetic repulsion arrangement, while FIG. 7B shows a magnetic attraction arrangement for another embodiment. In each case, a plate 110, with mounted magnets 112 and 114 is fixedly positioned to ground, i.e. the housing of the appliance, while plate 116 with magnets 118 and 110 is free to rotate as shown. A stator coil and drive assembly (not shown) rotates arm 122 which is connected to the moving plate 116. An output shaft 124 extends from arm 122, rotating with arm 122 to provide rotational work by means of a workpiece 126.

It is known that, unlike metal springs, magnets have a non-linear response, which can be disadvantageous in certain applications. In the above embodiments, a multiplicity of magnets can be used, or magnets of different strengths, to reduce the non-linear spring effect created by the magnets.

Accordingly, a magnetic spring arrangement for an oscillating resonant motor has been disclosed. The magnetic spring arrangement, with a stator and an AC drive circuit, produces the required oscillation for a desired linear stroke or a desired angle of rotation without mechanical springs. In this arrangement, the spring rate of the system is controllable by either adjusting the spacing of the magnets, i.e. the distance between the magnets, or by changing the size or strength of the magnets. This results in a change of amplitude of the linear stroke or rotational motion at a given drive frequency. The motor can produce either linear or rotational output motion to accomplish a variety of specific applications. In addition to rotational and linear output modes, the arrangement can be used to operate as a pump, with one or more inputs and outputs with valves on opposing sides of moving magnets, such as in the embodiments of FIGS. 1-3. The pump can move fluid in either or both directions of the stroke of the moving magnet.

Although preferred embodiments of the above-identified application have been disclosed for purposes of illustration, it should be understood that various changes, modifications and substitutions may be incorporated in the embodiments without departing from the spirit of the invention which is defined by the claims which follow.

What is claimed is:

1. A resonant linear motor, using a magnetic spring system, comprising:
   a housing having opposed first and second ends;
   a first magnet fixedly positioned at the first end of the housing and a second magnet fixedly positioned to the second end of the housing, the first and second magnets comprising permanent magnets, the first magnet having an opening;
   two movable magnets positioned in the housing for movement toward and away from each of the first and second magnets in a reciprocal, oscillating motion, wherein polarities of the two movable magnets oppose the polarities of an adjacent one of the first and second magnets and each of the two movable magnets is movable in relation to each other of the two movable magnets;
   an actuator arm attached to one of the two movable magnets which extends out through the opening, for linear movement thereof, in response to a driving action for the resonant linear motor; and
   a drive assembly which comprises a coil wrapped around an exterior of the housing and configured to drive the two movable magnets separately in opposing directions, wherein the two movable magnets are configured with opposing polarities, such that, in operation of the motor, vibration otherwise produced by the movement of the moving magnets is substantially cancelled.

2. The motor of claim 1, further comprising an AC drive signal source connected to the coil.

3. The motor of claim 2, wherein a frequency of the AC signal is substantially the same as a resonant frequency of a spring mass portion of the motor.

4. The motor of claim 1, including a linear bearing between the one of the two moving magnets and the housing.

5. The motor of claim 1, wherein the first magnet comprises a ring magnet having the opening through which the actuator arm extends.

6. The motor of claim 5, wherein the actuator arm includes a workpiece assembly comprising a brushhead for cleaning of teeth.

7. The motor of claim 1, wherein the coil wrapped around the exterior of the housing is further configured to drive the two movable magnets in opposing directions to each other so that vibration produced by movement of the moving magnets is substantially cancelled.

* * * * *